(12) United States Patent
Lee et al.

(10) Patent No.: US 9,259,162 B2
(45) Date of Patent: Feb. 16, 2016

(54) WIRELESS MONITORING SYSTEM FOR DETECTING BIO-SIGNAL ANALYSIS END DEVICE AND BIO-SIGNAL DETECTION END DEVICE

(71) Applicant: Shuenn-Yuh Lee, Tainan (TW)

(72) Inventors: Shuenn-Yuh Lee, Tainan (TW);
Jia-Hua Hong, Keelung (TW);
Cheng-Han Hsieh, Taichung (TW);
Ming-Chun Liang, Tainan (TW)

(73) Assignee: Shuenn-Yuh Lee, Tainan (TW)

( * ) Notice: Subject to any disclaimer, the term of this patent is extended or adjusted under 35 U.S.C. 154(b) by 54 days.

(21) Appl. No.: 14/109,703

(22) Filed: Dec. 17, 2013

(65) Prior Publication Data
US 2015/0005656 A1     Jan. 1, 2015

(30) Foreign Application Priority Data

Jun. 26, 2013   (TW) .............................. 102122868 A (51) Int. Cl.
*A61B 5/0428* (2006.01)
*A61B 5/0245* (2006.01)
*A61B 5/00* (2006.01)

(52) U.S. Cl.
CPC ............. *A61B 5/0245* (2013.01); *A61B 5/0022* (2013.01); *A61B 5/0428* (2013.01)

(58) Field of Classification Search
CPC ............................ A61B 5/0245; A61B 5/0428
See application file for complete search history.

(56) References Cited

U.S. PATENT DOCUMENTS

2011/0066053 A1\*  3/2011  Yazicioglu ................... 600/509

\* cited by examiner

*Primary Examiner* — George Evanisko
(74) *Attorney, Agent, or Firm* — Chun-Ming Shih (57) ABSTRACT

A wireless monitoring system for receiving, processing, wirelessly communicating and displaying bio-signal information is provided, inclusive of an analog front-end detection circuit with CHS (Chopper Stabilization) and sigma-delta modulation techniques, a digital signal processor (DSP) with disease identification capability, a digital controller with functions of encoding/decoding (CODEC), modulation/demodulation (MODEM) and data loss prevention in communication, and a wireless radio frequency (RF) transceiver with super-regenerative technique. The system can detect the real-time bio-signal and transmit the bio-signal data to the server by wireless communication. If the wireless communication is disconnected, the system would immediately store the data until the communication is reconnected. Therefore, the stored data will not be lost and can be transmitted with the real-time data as the communication is re-established. Moreover, the invention provides a bio-signal analysis end device and a bio-signal detection end device.

16 Claims, 3 Drawing Sheets

WIRELESS MONITORING SYSTEM FOR DETECTING BIO-SIGNAL ANALYSIS END DEVICE AND BIO-SIGNAL DETECTION END DEVICE

CROSS-REFERENCE TO RELATED APPLICATIONS

This application claims the priority of Republic of China Patent Application No. 102122868 filed on Jun. 26, 2013, in the State Intellectual Property Office of the R.O.C., the disclosure of which is incorporated herein by reference.

BACKGROUND OF THE INVENTION

1. Field of the Invention

The invention relates to a wireless monitoring chip system for detecting bio-signal in real time.

2. Descriptions of the Related Art

With the development of biomedical IC (Integrated Circuit), various circuits related to bio-signal detection and disease identification play an important role. Conventional bio-signal detection systems include basically analog front-end circuits and wireless transmission circuits, wherein the analog front-end circuits usually include preamplifiers, filters and analog to digital converters.

The bio-signal, such as heartbeat, in the biomedical field usually belongs to a low frequency signal. However, in low frequency application, because of the impact of flicker noise, the entire analog front-end circuit usually cannot achieve high resolution, such that the accuracy of the detection result is influenced and thereby the determination of medical personnel is misled, and the reliability is insufficient in diagnosis.

Additionally, the entire performance is often limited to specific elements because of there are a large amount of elements used.

Furthermore, the wireless RF (Radio Frequency) circuit usually plays a key role with respect to the entire power consumption. The use of conventional I/Q structure for RF circuit design increases power consumption considerably and reduces the service life.

Moreover, conventional systems do not process the detected bio-signal in advance prior to transmission to medical personnel. Therefore, signal transmission security and data loss are also important issues of bio-signal wireless transmission.

In conclusion, conventional bio-signal detection systems suffer from shortages such as insufficient reliability, poor performance, large power consumption, and/or low security. It is the goal of those skilled in the art to eliminate or mitigate these shortages to provide people with better user experience.

SUMMARY OF THE INVENTION

In view of the shortages of insufficient reliability, poor performance, large power consumption, and/or low security of conventional bio-signal detection systems, as for above problems, the inventor of the invention has strived to develop a wireless monitoring system for detecting bio-signal capable of detecting, analyzing and transmitting the bio-signal in wireless manner to achieve the effect that medical personnel (near end) may monitor the physical condition of examinees (fitting end). The wireless monitoring system of the invention may include: an analog front-end detection circuit, a fitting end digital signal processor, a fitting end digital data controller, and a fitting end wireless RF transceiver.

The analog front-end detection circuit may be used to process the bio-signal for generating a time domain digital detection data, and may have functions of chopper stabilization and sigma-delta modulation. The utilization of the chopper stabilization technique to convert the signal from low frequency (<1 kHz) to middle/high frequency (10 kHz~10 MHz) may avoid the impact flicker noise, and omit analog filter hardware to achieve the low power consumption requirement at the examinee end. Moreover, the utilization of sigma-delta modulation may gain high resolution digital signal for detecting various physical signals, such as heartbeat signal, brainwave signal etc. In addition, the modulated signal introduces quantization noise such that conventional Nyquist Rate Analog-to-Digital Converters are unnecessary for bio-signal acquisition with the effect of information security. Therefore, compared with conventional analog front-end circuit systems, the wireless monitoring system for detecting bio-signal of the invention is characterized in low power consumption, low complexity, high resolution and information security.

The fitting end digital signal processor is connected to the analog front-end detection circuit for receiving the digital detection data and generating frequency domain spectral transform coefficients, and has functions of disease identification and digital filter. Additionally, the fitting end digital signal processor may not only provide a digital decimation filter function to perform sigma-delta analog to digital conversion, but also comprise the function disease identification (for example, Wavelet Transform, Hilbert-Huang Transform) with feature extraction and classification. The parameters necessary for disease identification may be adjusted by a doctor at the monitoring end to increase disease identification rate, such that not only abnormal phenomena of bio-signals may be monitored and reflected in real time, but also the data amount for wireless transmission may be reduced to further reduce the power consumption of the system if only the feature parameters are transmitted.

Codec (Coding/Decoding) and modulation/demodulation mechanisms in communication technology may facilitate to eliminate or mitigate problems such as degradation, interference and the like for signal in transmission channels. The fitting end digital data controller is connected to the analog front-end detection circuit for receiving, coding and modulating the digital detection data, or is connected to the fitting end digital signal processor for receiving the spectral transform coefficients to generate wireless detection data. The possibility of communication data loss may be eliminated or reduced by coding and modulating.

The fitting end digital data controller is one of the characteristics of the invention. In addition to the digital modulation/demodulation and coding/decoding technologies necessary for communication baseband as illustrated above, a core FSM (Finite State Machine) and related controller may also be provided to determine decoded signal for supporting bio-signal output, spectral coefficients output, symptom code output, symptom parameters input and memory control. The fitting end digital data controller may further determine whether or not the wireless transmission runs normally. As the wireless transmission system is interrupted, the system will retain the data during the interruption period to prevent the data from loss. However, if the interruption period of the wireless transmission is too long, large memory capacity is necessary to retaining data during the interruption period such that not only the chip area is increased, but also more power is consumed. According to the result of the study of clinic doctors, a digital signal processor with disease identification function may be added in front of the digital controller system to store only abnormal bio-signals if the interruption period is too long for doctors to diagnose, thereby space and power consumption of memories may be reduced considerably.

The fitting end wireless RF transceiver is connected to the fitting end digital data controller for receiving and processing the wireless detection data and generating and transmitting a RF detection signal.

Because the bio-signal generally belongs to low frequency signal, the circuit may be subjected to the interference of flicker noise in process. Therefore, the analog front-end detection circuit may include a CHS (Copper Stabilization) circuit to convert the bio-signal from low frequency signal into middle/high frequency signal, such that not only the impact due to flicker noise may be reduced, but also the requirement of analog filter may be omitted, and thereby the effects of system resolution increase and power consumption reduction may be achieved.

The general wireless monitoring system for bio-signal detection may not have encryption/decryption mechanism and is subjected to the risk of information leakage in wireless transmission; while a system equipped with encryption/decryption mechanism suffers from limited space, large power consumption and reduced entire system performance because of the installation of encryption/decryption circuit. It is often a dilemma with respect to whether or not a wireless monitoring system for bio-signal detection is to be provided with encryption/decryption function. Because the sigma-delta modulator may introduce quantization noise inherently in analog to digital conversion for the digital data to have security effect in transmission and thus to have privacy for signal wireless transmission improved, the analog front-end detection circuit of the invention may include a high pass sigma delta modulator for the digital detection data to be introduced with quantization noise and have security effect. Thus, compared to conventional encryption technologies, the effects of not only the smaller necessary space, but also lower power consumption and higher performance may be achieved.

The fitting end digital signal processor may have a heartbeat detector for converting the spectral transform coefficients into heartbeat data.

The fitting end digital signal processor may have a spectra analysis coefficient register for registering and transmitting timely the spectral transform coefficients.

The fitting digital signal processor may have a symptom evaluator to generate target symptom codes according to the spectral transform coefficients.

Conventional physiological detection system may often lose important information, for example instant abnormal heartbeat phenomena, due to incomplete data transmission once instable transmission condition is encountered in real time transmission. To solve the problem of important information loss due to instable transmission, the fitting end digital data controller of the invention may have a retaining memory for storing the spectral transform coefficients, and may further provide a set of mechanism to detect whether or not the wireless transmission is in normal communication. As the wireless transmission is instable, the detection end may activate the storage function to store the bio-signals in the retaining memory as the wireless transmission is instable and interrupted, and transmit complete bio-signals once the wireless transmission is rebuilt.

Conventional wireless RF transceivers utilize feedback signals for signal process and suffer from increased complexity and large power consumption. The fitting end wireless RF transceiver may have a VCO (Voltage Controlled Oscillator) and may transmit RF detection signals with super-regenerative technology. Therefore, the effects of reduced complexity and smaller power consumption are achievable in comparison with conventional wireless RF transceivers.

The fitting end wireless RF transceiver may receive RF instruction signals and generate wireless instruction data, and the fitting end digital data controller may have a demodulator and a decoder for demodulating and decoding the wireless instruction data to generate the instructions.

The fitting end digital signal processor has a symptom evaluator for modifying symptom parameters or symptom weights according to the instructions.

The wireless monitoring system may further have a near end wireless RF transceiver for receiving the RF detection signals and restoring the wireless detection data, or transmitting the RF instruction signals; and a near end digital data controller connecting to the near end wireless RF transceiver for receiving the wireless detection data and restoring the digital detection data, or receiving the instructions to generate and transmit the wireless instruction data to the near end wireless RF transceiver.

The structure of the near end wireless RF transceiver may be identical to that of the fitting end wireless RF transceiver.

The wireless monitoring system of the invention may further have a near end digital signal processor connecting to the near end digital data controller for receiving the digital detection data and outputting bio-data corresponding to the bio-signal to be displayed on a monitor for medical personnel to diagnose.

Medical personnel may still need to observe time domain data. The near end digital signal processor may have an inverse spectral converter for transforming the wireless detection data from frequency domain data into time domain data.

The near end digital signal processor may have a symptom parameter output register capable of generating symptom information according to the wireless detection data for providing medical personnel with the symptom information generated automatically by the invention as reference.

The near end digital signal processor may have a CHS circuit and a decimation filter capable of modulating the wireless detection data from middle/high frequency to low frequency and filtering out the quantization noise, and thus restoring the digital detection data for medical personnel to reference.

Moreover, the invention further discloses a bio-signal analysis end device, including: an analysis end wireless RF transceiver, an analysis end digital data controller and an analysis end digital signal processor. The analysis end wireless RF transceiver is used to receive RF detection signals from outside and restore the wireless detection data, or transmit RF instruction signals generated locally. The analysis end digital data controller is connected to the analysis end wireless RF transceiver for receiving the wireless detection data and restoring to the digital detection data, or receiving control instruction from outside to generate and transmit wireless instruction data to the analysis end wireless RF transceiver, for the analysis end wireless RF transceiver to process the wireless instruction data and result in and transmit the RF instruction signals. The analysis end digital signal processor is connected to the analysis end digital data controller for receiving the wireless detection data and outputting the bio-data corresponding to the bio-signal.

Furthermore, in conjunction with the above bio-signal analysis end device for use, the invention further discloses a bio-signal detection end device, including: an analog front end detection circuit, a detection end digital signal processor, a detection end digital data controller and a detection end wireless RF transceiver. The analog front end detection circuit is used for processing the bio-signal to generate time domain digital detection data. The detection end digital signal processor is connected to the analog front-end detection circuit for receiving the digital detection data and generating frequency domain spectral transform coefficients. The detection end digital data controller is connected to the analog front end detection circuit for receiving, coding and modulating the digital detection data, or is connected to the detection end digital signal processor for receiving the spectral transform coefficients to generate wireless detection data to be transmitted. Moreover, the detection end wireless RF transceiver is connected to the detection end digital data controller for receiving and processing the wireless detection data to be transmitted to result in the RF detection signal for the analysis end wireless RF transceiver to receive.

In conclusion, the bio-signal detection wireless monitoring system or the bio-signal detection end device of the invention integrate the analog front-end detection circuit, the digital signal processor, the digital data controller, and the wireless RF transceiver, and may detect and transmit, in wireless manner, the bio-signal in real time to the monitoring end (the bio-signal analysis end device of the invention). The monitoring end may also modify parameters of the fitting end system (the bio-signal detection end device of the invention) by wireless transmission. If the wireless transmission end is disconnected (interrupted), the memory in the detection end may also be used to store the data during the disconnection period for the data in the disconnection period to be sent out as connection is rebuilt.

Compared to conventional technologies, identification parameters of the disease identification function may be adjusted by professional medical personnel, such as doctors, to facilitate diagnosis, shorten diagnosis time and improve diagnosis accuracy. The invention may be a SOC (System on Chip) at the fitting end (bio-signal detection end device) on examinee side, a portable device at the near end (bio-signal analysis end device) on medical personnel side, for example, watch, smart phone, personal mobile assistant, computer, set top box etc, and therefore, the effect of wearing for physiological monitoring at any time to achieve on body guard is available.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

The bio-signal detection wireless monitoring system provided in the invention may include a fitting end device on examinee side and a near end device on medical personnel side. The fitting end device and the near end device deliver control signals and data in wireless communication manner to avoid messy connection configuration between wired communication devices. Medical personnel utilize the near end device to monitor bio-signals from an examinee detected by the fitting end device.

Figure 1:
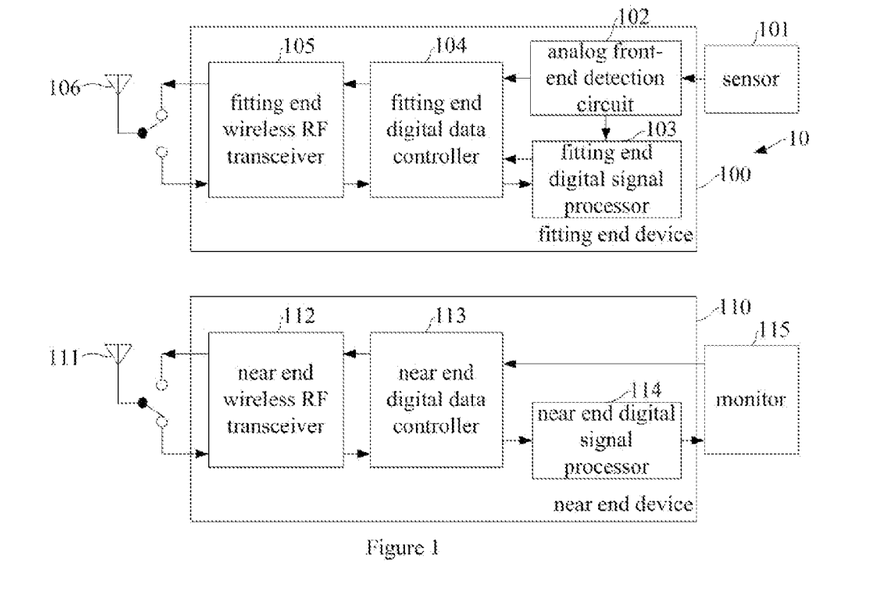
FIG. 1 is a block diagram showing a system basic structure of a bio-signal detection wireless monitoring system according to the invention.

Refer to FIG. 1, and it is a block diagram showing a system basic structure in an embodiment of the bio-signal detection wireless monitoring system according to the invention. As shown in FIG. 1, the bio-signal detection wireless monitoring system 10 of the invention may include devices located on the examinee side and the medical personnel side, and a wireless transmission channel (not shown). The device on the examinee side may include a sensor 101, a fitting end antenna 106, and a fitting end device 100 containing an analog front-end detection circuit 102, a fitting end digital signal processor 103, a fitting end digital data controller 104 and a fitting end wireless RF transceiver 105. Therefore, the fitting end device 100 may be defined as bio-signal detection end device. The device on the medical personnel side may include a monitor 115, a near end antenna 111, and a near end device 110 containing a near end wireless RF transceiver 112, a near end digital data controller 113 and a near end digital signal processor 114. Therefore, the near end device 110 may be defined as a bio-signal analysis end device.

The sensor 101 detects bio-signals of the examinee, such as heartbeat signal, brainwave signal, electromyographic signal, breathing signal etc., but not limited thereto, and transmits the detected bio-signals to the fitting end device 100 for process. Particularly, the bio-signal, the examinee and the medical personnel herein are conceptual terms. The bio-signal may be any signal to be detected by a sensing element. The examinee may be a biological entity or a non-biological entity with any feature, for example, such as heat and the like. The medical personnel may be a person or even an automatic machine that can monitor signals. Any system or devices, elements, means or methods therein that may detect signals by a sensor 101, process signals and/or transmit signals with the utilization of the invention falls within the scope of the invention. The sensor 101 may be a single function sensing element capable of detecting only one type of signal, or may be an integrated sensing element capable of detecting various signals. The sensor 101 may be a stand-alone device or may be integrated with the fitting end device 100.

The analog front-end detection circuit 102 of the fitting end device 100 has functions of CHS technology and sigma-delta modulation for converting the bio-signal from the sensor 101 into digital detection data, and transmitting the digital detection data to the fitting end digital data controller 104.

The fitting end digital data controller 104 receives the digital detection data from the sensor 101, and performs coding/decoding and modulation/demodulation processes to prevent data from loss in the wireless transmission channel as transmission, followed by generating and transmitting the wireless detection data to the near end wireless RF transceiver

105. The wireless detection data is transmitted to the medical personnel in a RF detection signal form by the fitting end wireless RF transceiver 105 and the fitting end antenna 106. The fitting end antenna 106 may be a stand-alone device or may be integrated with the fitting end device 100.

The near end antenna 111 on the medical personnel side receives and transmits the RF detection signal to the near end wireless RF transceiver 112. The near end wireless RF transceiver 112 converts down the frequency of the RF detection signal to restore and transmit wireless detection data to the near end digital data controller 113. The near end digital data controller 113 restores the digital detection data with demodulation and decoding functions therein. The digital detection data is transmitted to the near end digital signal processor 114 for processes of frequency down conversion and filtering out quantization noise to generate bio-data corresponding to the bio-signal on the examinee side. The bio-data is transmitted to the monitor 115. The medical personnel utilize the monitor 115 to identify the biological condition of the examinee with the received bio-data and adjust as need the mechanism of the bio-signal detection wireless monitoring system. In addition, the monitor 115 is a wide-sense concept of HMI (Human Machine Interface), which may not only output data in, for example, a display manner, but also have an element with input function such as touch panel or keyboard etc. for data input. Additionally, the monitor 115 may also be an automatic device, for example, such as a programmable server, by which instructions may be received, determined and processed and/or transmitted according to the bio-data.

As the medical personnel recognize that the mechanism of the bio-signal detection wireless monitoring system has to be adjusted, the monitor 115 may be utilized to transmit the modified symptom parameters to the fitting end device 100 through the near end digital data controller 113, the near end wireless RF transceiver 112, the near end antenna 111, the wireless transmission channel, and the fitting end antenna 106, thereby the control with respect to, for example, parameter modification or signal output format is performed to achieve the purpose of adjusting the bio-signal detection wireless monitoring system, as explained in more detail hereinafter.

In addition, the digital detection data, which is a time domain signal, may also be transmitted to the fitting end digital signal processor 103 by the analog front-end detection circuit 102 to allow the fitting end digital signal processor 103 to perform disease identification process such as wavelet transform, Hilbert Huang Transform etc. for the digital detection data, and thereby to reduce data transmission amount and filter out mains interference effect. Besides, the medical personnel may utilize the monitor 115, together with the identification result with respect to the biological condition and the adoption of suitable identification algorithm, to adjust the bio-signal detection wireless monitoring system in the communication transmission manner as mentioned above for improving disease identification rate and providing the examinee with customized diagnosis treatment.

Figure 2:
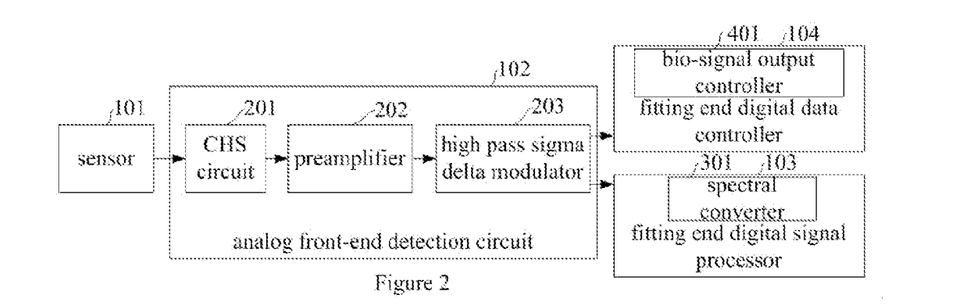
FIG. 2 is a block diagram showing a basic structure of an analog front-end detection circuit as illustrated in FIG. 1.

Based on the requirement and trend of product miniaturization, the bio-signal detection wireless monitoring system of the invention may be implemented as an IC (Integrated Circuit) by semiconductor technology. However, the so called flicker noise may occur in various transistor elements of the IC when used in low frequency application because, for example, some charges expected to flow in the channel between the source and the drain of a transistor may penetrate into the insulation film of the gate and thereby induce charge recombination. Additionally, the bio-signal output from the sensor 101 may also be not only weak, but also influenced by noise. Therefore, the bio-signal may need process by the analog front-end detection circuit 102 before effective information may be retracted. Refer to FIG. 2 now, and it is a block diagram showing a basic structure of an analog front-end detection circuit in an embodiment of the bio-signal detection wireless monitoring system according to the invention. As shown in FIG. 2, the analog front-end detection circuit 102 may include a CHS circuit 201, a preamplifier 202 and a high pass sigma delta modulator 203. Because the bio-signal may be ranged in low frequency range, for example, the frequency range smaller than 1 kHz, and be easy to be interfered by, for example, flicker noise, the invention utilizes the CHS circuit 201 to modulate the low frequency bio-signal to a middle/high frequency range, for example, from 10 kHz to 10 MHz in advance, followed by using the preamplifier 202 for amplification and modulation to be a middle/high frequency bio-signal to meet the dynamic range necessary for the subsequent high pass sigma delta modulator 203, followed by utilizing the high pass sigma delta modulator 203 to modulate the bio-signal that has been modulated to middle/high frequency and amplified to the digital detection data and output to the spectral converter 301 in the fitting end digital signal processor 103 and the bio-signal output controller 401 in the fitting end digital data controller 104. There is explanation in more detail hereinafter. Because the signal carrying the digital detection data has been in middle/high frequency range instead of a low frequency signal, the impact of the flicker noise in IC on the bio-signal detection may be reduced effectively. Moreover, a general sensing system utilizes analog filter to process the bio-signal provided by the sensor, while the analog filter often dominates the resolution of the entire system and consumes larger power. Therefore, in the analog front-end detection circuit 102 of the invention, the high pass sigma delta modulator 203 is utilized for modulation and generating digital detection data with quantization noise, such that the function similar to encrypted frequency spreading is available. Thus, the requirement of analog filter element may be eliminated while the resolution of the bio-signal detection system may be increased and the power consumption may be reduced.

Figure 3:
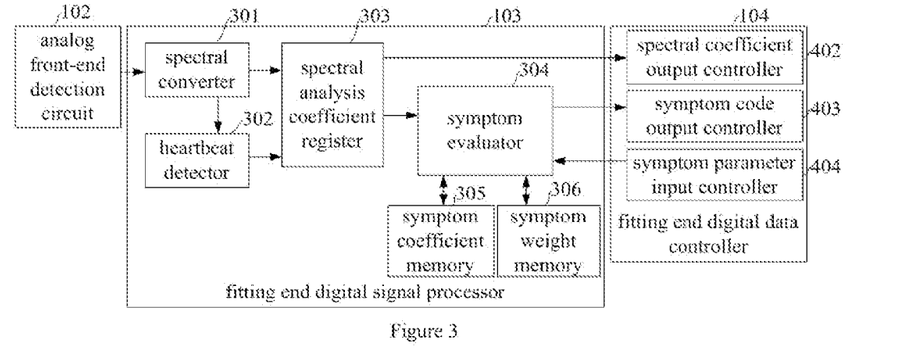
FIG. 3 is a block diagram showing a basic structure of a fitting end digital signal processor as illustrated in FIG. 1.

For conventional sensing systems, the time domain signals sensed at various time points are transmitted sequentially. Such manner may not only consume large transmission power consumption, but also cause the system not able to transmit signals in real time because, for example, the noise is too large that results in system reboot, and thereby important messages may be lost. Therefore, the fitting end digital signal processor 103 of the invention utilizes disease identification technology to solve existing problems of conventional sensing systems. Refer to FIG. 3, which is a block diagram that shows a basic structure of a fitting end digital signal processor in one embodiment of the bio-signal detection wireless monitoring system according to the invention. As shown in FIG. 3, the fitting end digital signal processor 103 may include: a spectral converter 301, a heartbeat detector 302, a spectral analysis coefficient register 303, a symptom evaluator 304, a symptom coefficient memory 305 and a symptom weight memory 306.

The digital detection data from the analog front-end detection circuit 102 is received by the spectra converter 301 in the fitting end digital signal processor 103. The spectral converter 301 performs algorithm, such as Wavelet Transform, Hilbert Huang Transform, or the like to generate the spectral transform coefficients, for example, wavelet transform coefficients. The spectral transform coefficients may be transmitted to the heartbeat detector 302 to generate heartbeat data for heartbeat period identification. The spectral transform coefficients generated by the spectral converter 301 and the heartbeat data generated by the heartbeat detector 302 are transmitted to the spectral analysis coefficient register 303, instead of being necessary to be sent to backend elements directly for process or wireless transmission, and thereby the power consumption caused by wireless communication transmission is reduced effectively.

Figure 4:
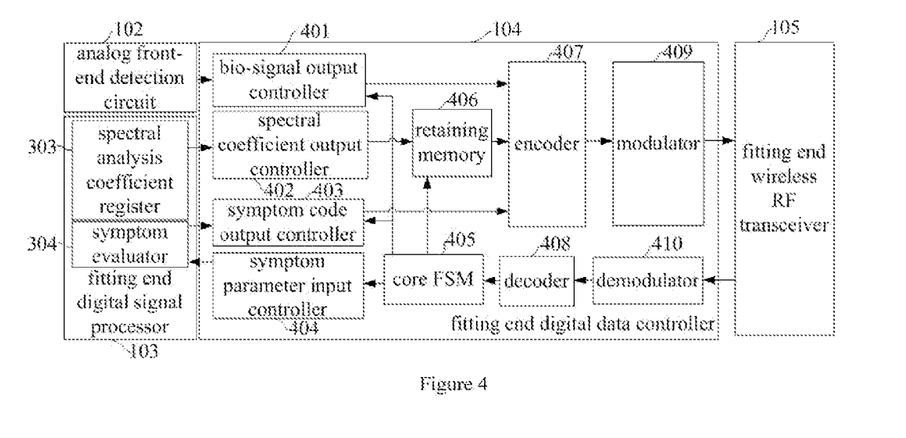
FIG. 4 is a block diagram showing a basic structure of a fitting end digital data controller as illustrated in FIG. 1.

The spectral analysis coefficient register 303 may transmit the spectral transform coefficients or the heartbeat data to a spectral coefficient output controller 402 (explained in more detail hereinafter) in the fitting end digital data controller 104, and thereby the fitting end wireless RF transceiver 105 is controlled to perform message wireless transmission.

Besides, the spectral analysis coefficient register 303 may further transmit the spectral transform coefficients to the symptom evaluator 304 for disease identification. The symptom evaluator 304 may utilize the spectral transform coefficients to determine whether or not an event to be analyzed occurs such as abnormal spectrum pattern due to, for example, over fast or over slow heartbeat, over small or over large heartbeat amplitude, or the like. Once an event to be analyzed is determined to occur, the symptom evaluator 304 receives a series of spectral transform coefficients with specific counts from the spectral analysis coefficient register 303, and performs sectional comparison with symptom parameters stored in the symptom coefficient memory 305 in advance. In performing sectional comparison, the series of spectral transform coefficients with the specific count and the symptom parameters from the symptom coefficient memory 305 are both regarded as curves, and are called spectral transform coefficient curve and symptom parameter curve hereinafter, respectively. If the intersected area of the spectral transform coefficient curve and the symptom parameter curve is smaller than a predetermined threshold value, the two curves are determined as proximate; otherwise, they are determined as unlike. Multiple symptom parameter curves may be stored in the symptom coefficient memory 305 for sectional comparison with the spectral transform coefficient curve. A specified symptom weight is provided for the symptom parameter curve with respect to two proximate curves from the sectional comparison. The scale of the symptom weight may be provided by the symptom weight memory 306. In all sectional comparisons, the symptom parameter curve with the largest symptom weight is determined as the target symptom, that is, the symptom the examinee might suffer from. The target symptom is indicated with a symptom code. The symptom code indicative of the target symptom is called target symptom code hereinafter. The target symptom code, according thereto, is determined whether or not to be transmitted to medical personnel for reference by the subsequent fitting end digital data controller 104, instead of transmitting the entire spectra transform coefficient curve. Alternatively, as transmitting the target symptom code, the corresponding spectral transform coefficients are transmitted to medical personnel together, instead of all detected bio-signals. Thus, unnecessary data transmission and the power consumption may be reduced considerably.

The symptom parameters stored in the symptom coefficient memory 305 and the symptom weights stored in the symptom weight memory 306 may be changed appropriately by the medical personnel with medication profession according to diagnosis result, literature data or the like, and thereby the invention may have an interactive structure capable of customizing symptom determination. Based on the interactive structure, the invention may reduce effectively the complexity of symptom determination and improve accuracy and effectiveness of system diagnosis, and is thus trusted by the medical personnel and the examinee. Different from conventional digital signal processors that need large hardware devices for very complex algorithm process and transmission of large amount of data to acquire very high disease identification rate and thus are not only expensive but also power consumed and heavy, the invention, in combination with professional knowledge of the medical personnel, may utilize the function of the fitting end digital signal processor 103 to change the symptom parameters and the symptom weights without complex symptom identification determination algorithm to provide the medical personnel with reliable symptom identification result in an efficient manner. The complexity of system design is reduced effectively. Additionally, the invention, in combination the monitor 115, utilizes software interactive diagnosis interface to develop professional diagnosis knowledge effectively, perform symptom parameter optimization flexibly, and thereby to improve the disease identification rate to assist the medical personnel in diagnosis.

In information delivery, wireless communication may have signal distorted due to noise interference in the wireless transmission channel. With channel coding, accuracy of signal transmission may be improved effectively. Available channel coding includes, for example, cyclic code, convolution code or the like, but the invention is not limited thereto. Refer to FIG. 4, which is a block diagram that shows a basic structure of a fitting end digital data controller in one embodiment of the bio-signal detection wireless monitoring system according to the invention. As shown in FIG. 4, the fitting end digital data controller 104 may include: a bio-signal output controller 401, a spectral coefficient output controller 402, a symptom code output controller 403, a symptom parameter input controller 404, a core FSM 405, a retaining memory 406, a encoder 407, a decoder 408, a modulator 409, and a demodulator 410. Besides of channel coding and decoding, the fitting end digital data controller 104 may further determine output formats of signals such as bio-signal, spectral transform coefficient and target symptom code, input format of symptom parameter, as explained in detail hereinafter.

The medical personnel may utilize the monitor 115 to send a control instruction to control the fitting end digital data controller 104. The control instruction passes through the wireless transmission channel, the fitting end antenna 106, the fitting end wireless RF transceiver 105 and enters the fitting end digital data controller 104, followed by being demodulated by the demodulator 410 and being decoded by the decoder 408 and being transmitted to the core FSM 405 to control operation of the fitting end digital data controller 104.

If the control instruction requests to extract bio-signal, the core FSM 405 may, according to the received control instruction, request the bio-signal output controller 401 to receive the digital detection data from the analog front-end detection circuit 102, the spectral coefficient output controller 402 to receive the spectral transform coefficients or heartbeat data from the spectral analysis coefficient register 303, and the symptom code output controller 403 to receive the target symptom code from the symptom evaluator 304, and request respectively the bio-signal output controller 401, the spectral coefficient output controller 402 and the symptom code output controller 403 to transmit the digital detection data, the spectral transform coefficients or the heartbeat data, and the target symptom code to the encoder 407 for coding, followed by requesting the demodulator 409 to perform demodulation and transmitting the result to the fitting end wireless RF transceiver 105 for transmitting to the medical personnel through the antenna 106.

If wireless communication interruption condition occurs in data transmission, the core FSM 405 instructs the retaining memory 406 to store the spectral transform coefficients, such that the spectral transform coefficients saved in the retaining memory and the digital detection data are output to the decoder 407 for subsequent wireless transmission after the wireless communication is recovered.

Besides, the core FSM 405 may also receive and transmit the control instruction carrying the symptom parameters and/or the symptom weight to be modified by the medical personnel to the symptom parameter input controller 404, followed by modifying the symptom parameters in the symptom coefficient memory 305 and/or the symptom weights in the symptom weight memory 306 by the symptom evaluator 304, and thereby customizing symptom identification principle of the medical personnel for the examinee to improve effectiveness and accuracy of symptom identification.

Data transmission manner is determined according to the control instruction received by the core FSM 405. For wireless transmission manner, the modulator 409 and the demodulator 410 may be implemented with means such as ASK (Amplitude Shift Keying), PSK (Phase Shift Keying), FSK (Frequency Shift Keying), or the like, but the invention is not limited thereto.

Figure 5:
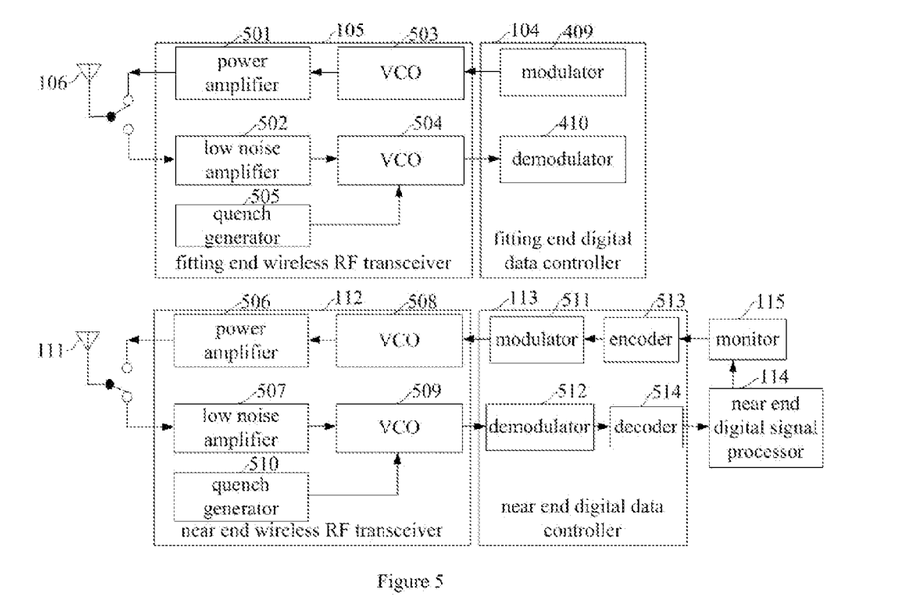
FIG. 5 is a block diagram showing structures of a fitting end wireless RF transceiver, near end wireless RF transceiver and a near end digital data controller as illustrated in FIG. 1.

A wireless RF circuit usually dominates power consumption in an entire SOC. If conventional I/Q modulation/demodulation structure is used to design wireless RF circuit of the near end wireless RF transceiver 112, the power consumption is increased considerably and the service life of the device is shortened because of the need of mixer and high gain amplifier for demodulation. To simplify wireless RF circuit hardware and reduce power consumption, the wireless RF circuit design of the invention does not use the conventional manner that uses negative/positive feedback manner to enhance signal, but uses a super-regenerative technique, in combination digital output and modulation technologies of the fitting end digital data controller to control directly VCO in the wireless RF circuit for high frequency carrier modulation to generate a carrier of, for example, ASK (Amplitude Shift Keying), PSK (Phase Shift Keying), FSK (Frequency Shift Keying), which is then amplified by a power amplifier and emitted by an antenna to the wireless channel; while the wireless RF circuit at the receiving end may utilize low noise amplifier and VCO to perform demodulation of digital data. Such technique is different from the I/Q modulation/demodulation technique used in existing wireless network devices, for example, WiFi, Bluetooth, ZigBee etc., and has considerably low complexity and power consumption to be suitable for portable and wearable bio-signal detection wireless monitoring system.

Refer to FIG. 5, which is a block diagram that shows a basic structure with a fitting end wireless RF transceiver, a fitting end digital data controller, a near end wireless RF transceiver and a near end digital data controller in one embodiment of the bio-signal detection wireless monitoring system according to the invention. As shown in FIG. 5, the fitting end wireless RF transceiver 105 includes: a power amplifier 501, a low noise amplifier 502, VCOs (503, 504), and a quench generator 505. The near end wireless RF transceiver 112 includes: a power amplifier 506, a low noise amplifier 507, VCOs (508, 509), and a quench generator 510. The near end digital data controller 113 includes: a modulator 511, a demodulator 512, an encoder 513 and a decoder 514.

The wireless detection data transmitted from the modulator 409 at the examinee end controls the VCO 503 to output an oscillation signal for the power amplifier 501 to generate the RF detection signal, which is transmitted to the wireless transmission channel through the antenna 106. The RF detection signal received by antenna 111 from the wireless transmission channel is transmitted to the low noise amplifier 507 in the near end wireless RF transceiver 112 for signal amplification. The amplified modulation signal may be processed and controlled by the VCO 509 and the quench generator 510 to restore the wireless detection data. The wireless detection data is demodulated by the demodulator 512 and decoded by the decoder 514 to output the digital detection data. The digital detection data is transmitted to the near end digital signal processor 114 for frequency down conversion and filtering process to restore the bio-data corresponding to the bio-signal and display on the monitor 115 for the medical personnel to diagnose.

As above, the medical personnel may determine whether to send the control instruction via the monitor 115 according to diagnosis result to control the fitting end device 100, such as, for example, bio-signal extraction, signal output format or symptom parameter modification etc., but the invention is not limited thereto. The control instruction of the medical personnel is decoded and demodulated by the decoder 513 and the demodulator 511 in the near end digital data controller 113 to become wireless instruction data via the monitor 115. The wireless instruction data is processed by the VCO 508 and the power amplifier 506 as a RF instruction signal form to be sent to the fitting end device 100 through the antenna 111, the wireless transmission channel and the antenna 106. The RF instruction signal from the antenna 106 is amplified by the low noise amplifier 502 in the fitting end wireless RF transceiver 105. The amplified signal is processed and controlled by the VCO 504, the quench generator 505 to restore the wireless instruction data. The wireless instruction data is transmitted to the fitting end digital data controller 104 for the demodulator 410 and the decoder to perform demodulation and decoding to restore the control instruction commanded by the medical personnel. The core FSM 405 receives the control instruction to perform control actions as above.

Figure 6:
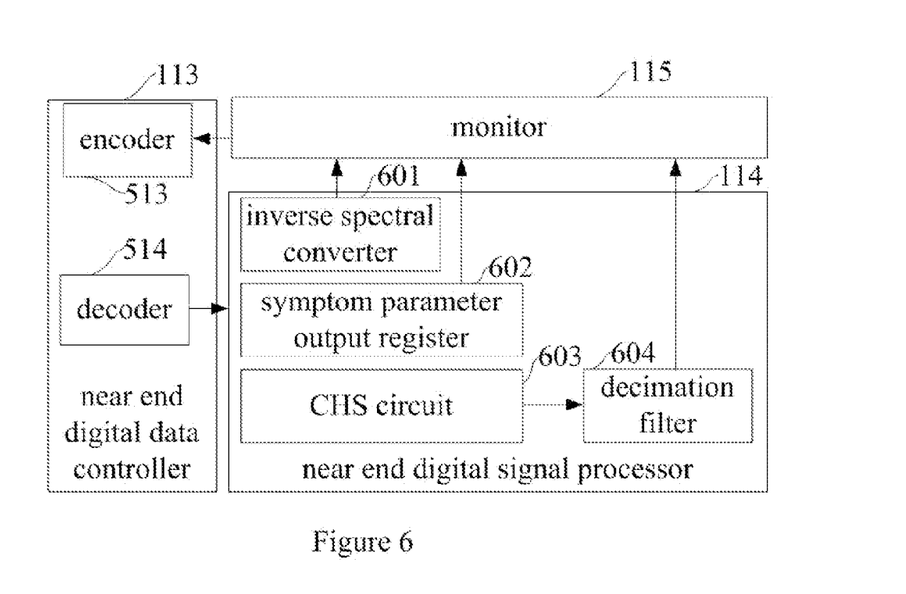
FIG. 6 is a block diagram showing a system basic structure of a near end digital signal processor as illustrated in FIG. 1.

To provide the user with real-time bio-signal monitoring and the medical personnel with disease diagnosis, the near end digital signal processor needs to have the capability of inverse spectral transform, for example, Inverse Wavelet Transform, and the capability of decimation filter, to restore the bio-data and display possible disease on the display. Refer to FIG. 6, which is a block diagram that shows a basic structure of a near end digital signal processor in one embodiment of the bio-signal detection wireless monitoring system according to the invention. In FIG. 6, the near end digital signal processor 114 includes: an inverse spectral converter 601, a symptom parameter output register 602, a CHS circuit 603 and a decimation filter 604. To restore the digital detection data output from the analog front-end detection circuit 102, the CHS circuit 603 may modulate the signal from middle/high frequency range (10 kHz~10 MHz) to low frequency range (<1 KHz), and the quantization noise may be filtered out by the decimation filter 604, at last, the digital detection data is restored and displayed on the monitor 115. Besides, the spectral transform coefficients from the fitting end digital signal processor 103 may be restored to time domain data from frequency data by the inverse spectral converter 601 and displayed on the monitor 115. Wherein, the target symptom code generated by the symptom evaluator 304 of the fitting end digital signal processor 103 may display the symptom on the monitor 115 through the symptom parameter output register 602 by, for example, table lookup, for medical personnel to reference.

Herein, with embodiments for explanation in detail, the bio-signal detection wireless monitoring system designed according to the invention may utilize advantages of the fitting end device (the bio-signal detection end device of the invention), including compactness, power saving, high resolution, disease identification and communication with medical personnel, and the near end device (the bio-signal analysis end device of the invention) may provide users or medical personnel with reference to perform bi-signal real-time monitoring and disease diagnosis. Those skilled in the art may utilize different communication protocols and circuit structure to implement the invention. For example, communication technologies such as NFC (Near Field Communication) or FFC (Far Field Communication) may be utilized to implement the invention. Thus, any simple modification of communication protocol and circuit structure for the invention should fall within the scope of the invention.

Additionally, for easy explanation, signal or data names used for communication between elements in the fitting end device 100 (the bio-signal detection end device of the invention) and the near end device 110 (the bio-signal analysis end device of the invention) may be the same. However, these are only exemplary embodiments. Those skilled in the art may adjust easily design or configuration of elements to differentiate signals or data between elements without departing from the scope of the invention from reading the contents disclosed in the invention.

What is claimed is:

1. A wireless monitoring system for detecting a bio-signal, including:
    an analog front-end detection circuit for processing said bio-signal to generate time domain digital detection data;
    a fitting end digital signal processor, which is connected to said analog front-end detection circuit for receiving said digital detection data and generating a frequency domain spectral transform coefficient;
    a fitting end digital data controller connected to said detection circuit and said signal processor, and which is either switched between said analog front-end detection circuit for receiving, coding and modulating said digital detection data to generate wireless detection data, or is switched to said fitting end digital signal processor for receiving said spectral transform coefficient to generate said wireless detection data; and
    a fitting end wireless RF (Radio Frequency) transceiver, which is connected to said fitting end digital data controller for receiving and processing said wireless detection data and generating and transmitting a RF detection signal based on said processed wireless detection data.

2. The wireless monitoring system of claim 1, wherein said bio-signal is a low frequency signal, and said analog front-end detection circuit includes a CHS (Chopper Stabilization) circuit for converting said bio-signal from the low frequency signal into a middle/high frequency signal.

3. The wireless monitoring system of claim 1, wherein said analog front-end detection circuit includes a high pass sigma delta modulator for modulating said digital detection data to carry quantization noise with security effect.

4. The wireless monitoring system of claim 1, wherein said fitting end digital signal processor has a heartbeat detector for converting said spectral transform coefficient into heartbeat data.

5. The wireless monitoring system of claim 1, wherein said fitting end digital signal processor has a spectral analysis coefficient register for registering and transmitting said spectral transform coefficient.

6. The wireless monitoring system of claim 1, wherein said fitting end digital signal processor has a symptom evaluator to generate a target symptom code according to said spectral transform coefficient.

7. The wireless monitoring system of claim 1, wherein said fitting end digital data controller has a retaining memory for storing said spectral transform coefficient.

8. The wireless monitoring system of claim 1, wherein said fitting end wireless RF transceiver has a VCO (Voltage Controlled Oscillator) that transmits said RF detection signal with a super regenerative technique.

9. The wireless monitoring system of claim 1, wherein said fitting end wireless RF transceiver is further used to receive a RF instruction signal transmitted from outside and generate wireless instruction data, and said fitting end digital data controller has a demodulator and a decoder for demodulating and decoding said wireless instruction data to generate a control instruction.

10. The wireless monitoring system of claim 9, wherein said fitting end digital signal processor stores a symptom parameter and a symptom weight, and said fitting end digital signal processor has a symptom evaluator for modifying said symptom parameter or said symptom weight according to said control instruction.

11. The wireless monitoring system of claim 9, further having:
    a near end wireless RF transceiver for either receiving the RF detection signal transmitted from said fitting end wireless RF transceiver and restoring said wireless detection data, or outputting the RF instruction signal for said fitting end wireless RF transceiver to receive; and
    a near end digital data controller, which is connected to said near end wireless RF transceiver for either receiving said wireless detection data and restoring said digital detection data, or receiving and transmitting said wireless instruction data for generating said control instruction to said near end wireless RF transceiver.

12. The wireless monitoring system of claim 11, further having a near end digital signal processor, which is connected to said near end digital data controller for receiving said digital detection data and outputting bio-data corresponding to said bio-signal.

13. The wireless monitoring system of claim 12, wherein said near end digital signal processor has an inverse spectral converter for converting said wireless detection data to time domain data.

14. The wireless monitoring system of claim 12, wherein said near end digital signal processor has a symptom parameter output register for generating symptom information according to said wireless detection data.

15. The wireless monitoring system of claim 12, wherein said near end digital signal processor has a CHS circuit and a decimation filter, said CHS circuit and filter for demodulating said wireless detection data with a middle/high frequency from the middle/high frequency to a low frequency and filtering out quantization noise.

16. A bio-signal detection end device adapted to be connected with a bio-signal analysis end device, said bio-signal detection end device including:
    an analog front-end detection circuit for processing said bio-signal to generate time domain digital detection data;
    a detection end digital signal processor, which is connected to said analog front-end detection circuit for receiving said digital detection data and generating a frequency domain spectral transform coefficient;
    a detection end digital data controller connected to said detection circuit and said signal processor, and which is either switched between said analog front-end detection circuit for receiving, coding and modulating said digital detection data to generate wireless detection data, or is switched to said detection end digital signal processor for receiving said spectral transform coefficient to generate said wireless detection data to be transmitted; and a detection end wireless RF transceiver, which is connected to said detection end digital data controller for receiving and processing said wireless detection data and generating and transmitting said RF detection signal based on said processed wireless detection data for said analysis end wireless RF transceiver to receive.

\* \* \* \* \*